(12) United States Patent
Jordan

(10) Patent No.: US 8,475,436 B1
(45) Date of Patent: Jul. 2, 2013

(54) SURGICAL INSTRUMENT WITH STEERABLE DIRECTIONAL SHAFT

(76) Inventor: Christopher Jordan, Midwest City, OK (US)

( * ) Notice: Subject to any disclaimer, the term of this patent is extended or adjusted under 35 U.S.C. 154(b) by 828 days.

(21) Appl. No.: 12/587,254

(22) Filed: Oct. 5, 2009

(51) Int. Cl.
*A61M 35/00* (2006.01)

(52) U.S. Cl.
USPC ................................. 606/1; 604/95

(58) Field of Classification Search
None
See application file for complete search history.

(56) References Cited

U.S. PATENT DOCUMENTS

| | | |
|---|---|---|
| 4,441,497 A | 4/1984 | Paudler |
| 4,719,924 A | 1/1988 | Crittenden |
| 4,874,376 A | 10/1989 | Hawkins, Jr. |
| 5,011,473 A | 4/1991 | Gatturna |
| 5,195,968 A * | 3/1993 | Lundquist et al. ......... 604/95.04 |
| 5,318,528 A | 6/1994 | Heaven |
| 5,350,391 A * | 9/1994 | Iacovelli ...................... 606/170 |
| 5,501,654 A * | 3/1996 | Failla et al. ................... 600/204 |
| 6,464,711 B1 | 10/2002 | Emans |
| 6,530,913 B1 | 3/2003 | Giba |
| 7,381,205 B2 | 6/2008 | Thommen |
| 2006/0079911 A1 | 4/2006 | Muramatsu |
| 2009/0177219 A1 | 7/2009 | Conlon |

* cited by examiner

*Primary Examiner* — Sam Yao
*Assistant Examiner* — Scott T Luan
(74) *Attorney, Agent, or Firm* — Randal D. Homburg

(57) ABSTRACT

A steerable surgical instrument provides a steerable tip guided through tissue in a pathway other than linear, the steerable surgical instrument having a fixed handle and a trigger which, when pushed downward, elevates the tip in an upward direction and when pulled towards the fixed handle, lowers the top in a downward allowing the steerable surgical instrument to be guided through tissue in a bi-directional curved pathway, resulting in a reduction of damage to collateral tissue during the surgical procedure.

12 Claims, 6 Drawing Sheets

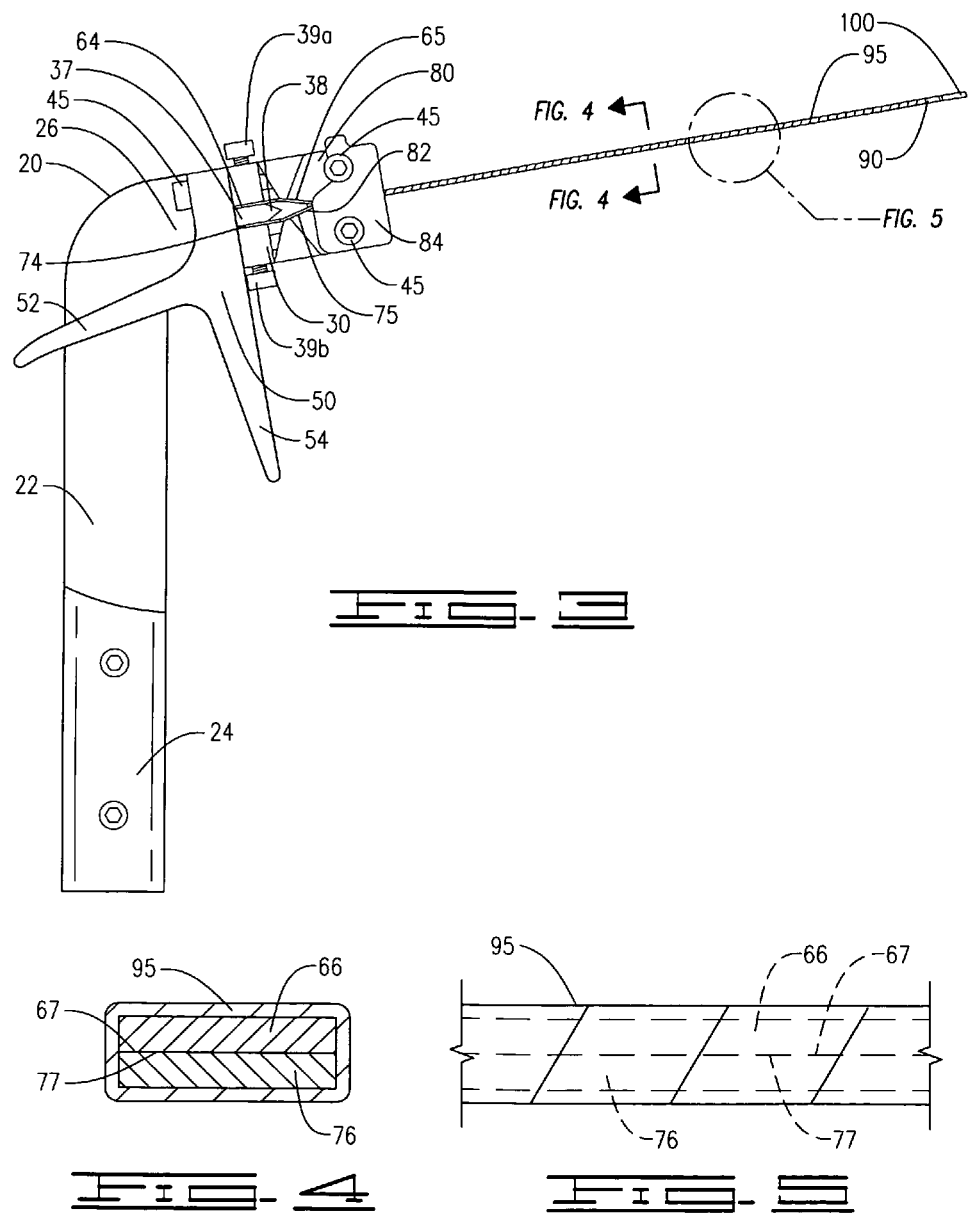

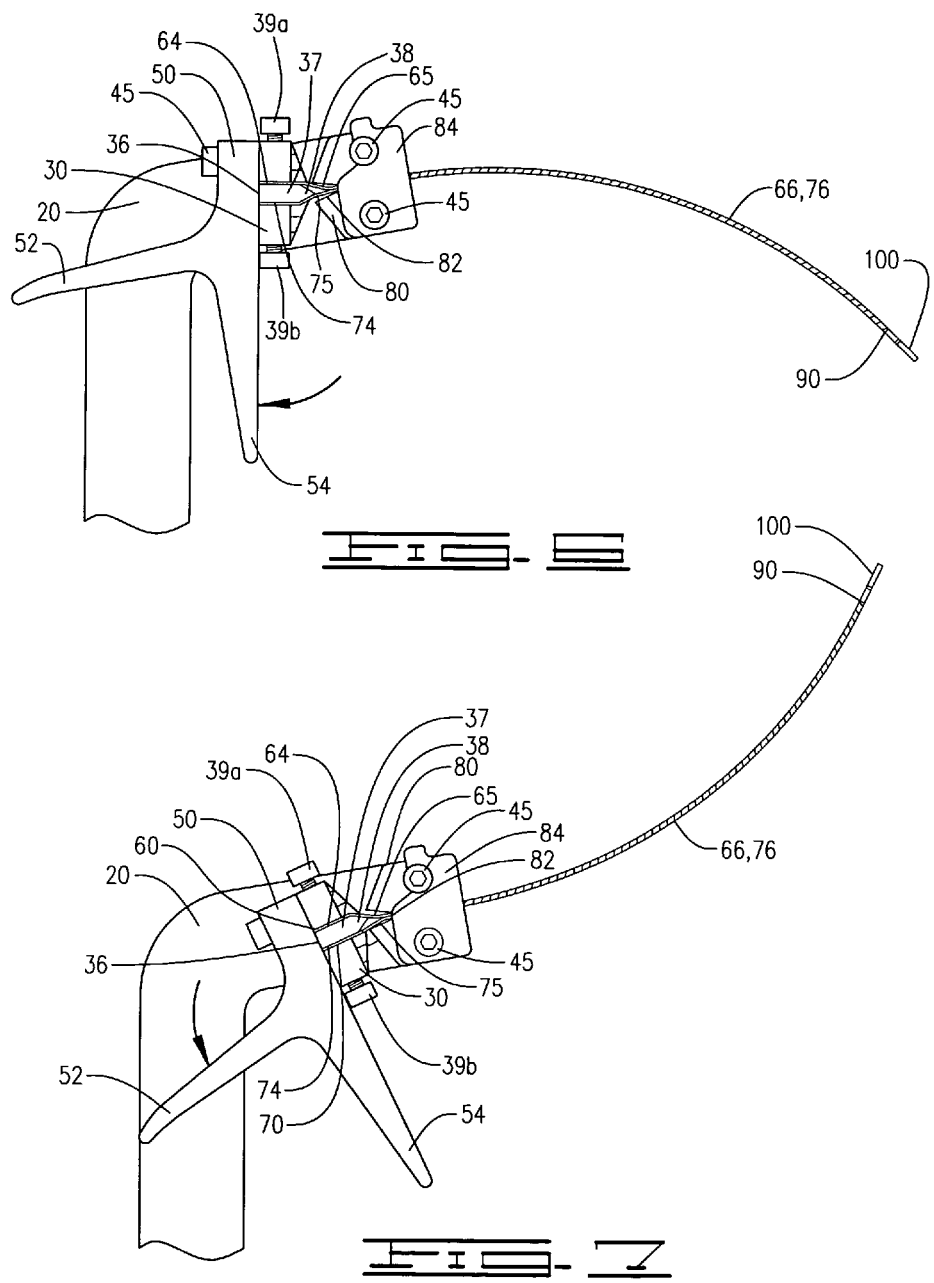

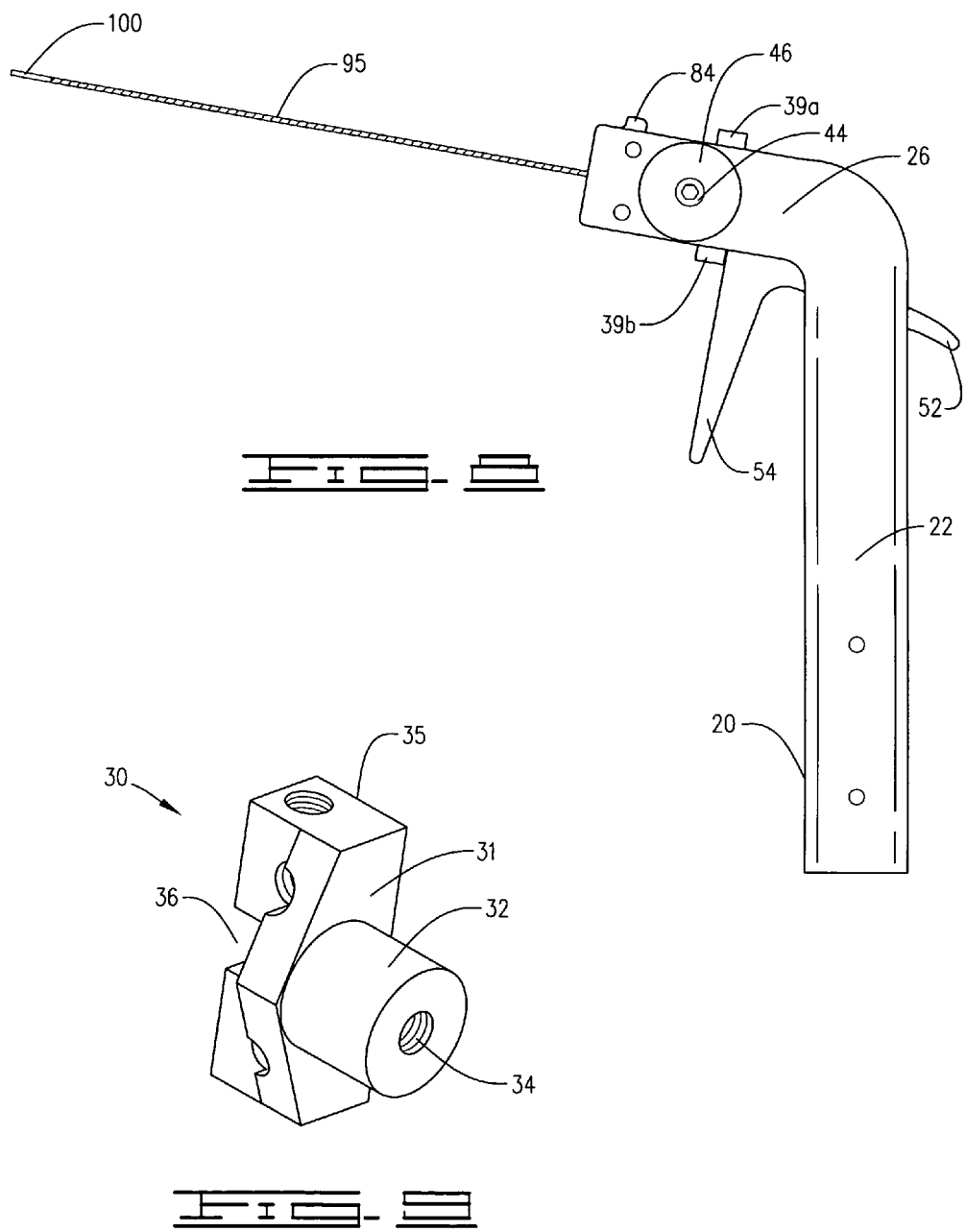

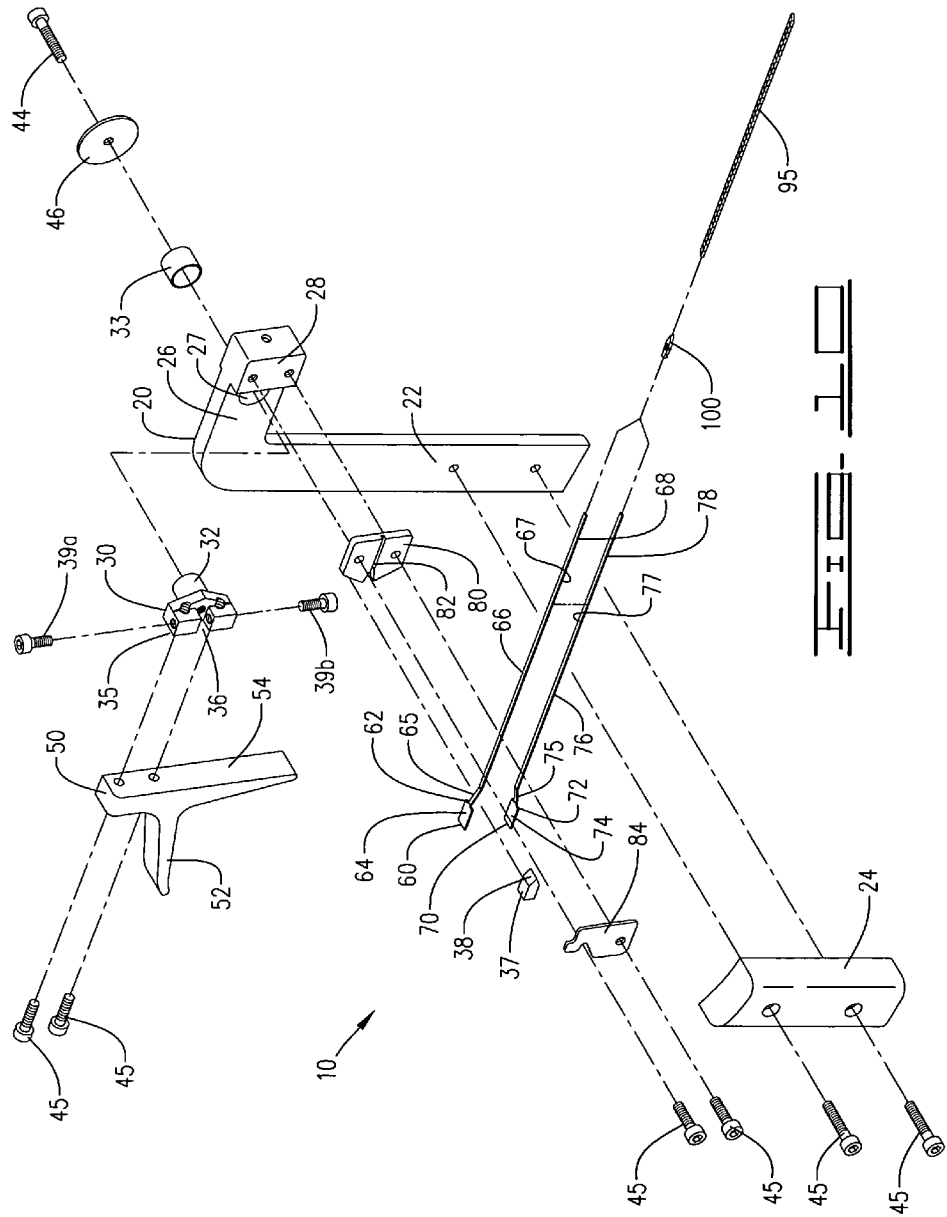

SURGICAL INSTRUMENT WITH STEERABLE DIRECTIONAL SHAFT

CROSS REFERENCE TO RELATED APPLICATIONS

Reference is made to a co-pending U.S. patent application Ser. No. 11/986,834, filed on Nov. 27, 2007, by the same inventor, Christopher Jordan.

I. BACKGROUND OF THE INVENTION

1. Field of Invention

Surgical instruments, primarily those associated with the application of sutures into internal tissues during the course of surgery, are provided with and handle extending an upper resilient member and lower resilient member having respective first ends clamped within an anchor plate with a wedged spacer between the first ends further attaching to a pivotal trigger and forming a handle portion, the upper and lower resilient members also defining respective second ends forming an operational end of the slidingly engaged and wrapped upper and lower resilient members further defining an operational end attaching a tool, wherein the pivotal trigger mechanism is pushed downward, an inward tension is applied to the upper resilient member with an outward force applied to the lower resilient member, forcing the second ends of the upper and lower members in an upward direction, and wherein the pivotal trigger mechanism is pulled back towards the handle, an inward tension is applied to lower resilient member with an outward force applied to the upper resilient member, forcing the second ends of the upper and lower members in a downward direction allowing the surgical instrument to be guided through tissue in a bi-directional curved pathway, resulting in a reduction of damage to collateral tissue during the surgical procedure.

2. Description of Prior Art

The following United States patents and publications were discovered and are disclosed within this application for utility patent. All relate to surgical instruments with some of them using a steering mechanism in some form or manner.

Several of the surgical instruments are shown by example, which may be adapted to the presently disclosed technology are provided for a brief reference as to the types of surgical instruments for which the improvements to the art as surgical instruments for sale and use by Inlet Medical Inc., disclosing suture passers, sutures, ligament graspers, tie knot pushers, clamps. Those references have not been included for review due to their having been removed from public access and thus not included by reference. They still have made reference to small surgical instruments to reduce the amount of collateral damage to surrounding tissue caused by their insertion into a surgical site.

Dr. Allen Deutsch, M.D., in an article written in the US Musculoskeletal Review 2006, pgs. 35-37, identifies the newer and smaller penetrating instruments used in a rotator cuff repair, and identifies factors to be considered in choosing surgical instruments for passing a suture through the rotator cuff, including: accuracy, its potential to cause further injury to degenerative cuff tissue, the amount of tissue that can be incorporated into the repair, and its cost. Again that reference cannot be supplied due to it having been removed from public access. The identified surgical instruments are suture punches and penetrating suture graspers. He further identifies two surgical instruments for this procedure as the Scorpion™, made by Arthrex of Naples, Fla., and the ExpressSew™, made by Mitek of Raynham, Mass.

U.S. Pat. No. 5,011,473 to Gatturna discloses a device for securing and positioning a wire to a needle, including a probe wire through a cannula needle and mor particularly, towards a locking and positioning device for a needle wire localizer. There is a J-curved tip next to the point of the needle. Another similar needle guide is indicated in U.S. Pat. No. 4,874,376 to Hawkins, Jr. An earlier suture passer is shown in U.S. Pat. No. 4,441,497 to Paudler, which has a plurality of elongated flexible members attached at two common ends forming dual piercing tips, with the suture placed between connected flexible members as the device is inserted into a surgical pathway, with the members bending around curves through manual manipulation.

A ligating device is shown in Patent Application Publication No. 2006/0079911 to Muramatsu, which demonstrates an introduction tube inserted into a location within the surgical site with at least two manipulating wires movably inserted within the tube and at least two clips having a proximal end portion with a pinch section at the end of the tube. The wires manipulate the clips within the tube with the clips having the ability to grasp tissue and pull it within the tube. A suture passer with a curved suture carrier with a sharpened tip, shown with two suture passers, allow for the upward insertion of sutures from below and insertion level for passing and directing the sutures upwards through tissue after piercing the tissue from above.

In U.S. Pat. No. 4,719,924 to Crittenden, a steerable guide wire provides the means to adjust the curvature of the tip of a surgical instrument during a cardiovascular surgical procedure. An inner tubular member rotating inside an outer tubular member provides the means for rotation of a surgical instrument, with an arthroscopic grasper mounted on the end of the outer member, disclosed in U.S. Pat. No. 5,318,528 to Heaven. A pull cable inside a catheter inserted into an artery and extended into the heart, specifically during a transmyocardial revascularization procedure, is use to steer the tip of the instrument through the artery, the pull cable at the handle portion of the instrument as disclosed in U.S. Pat. No. 6,530,913 to Giba. In U.S. Pat. No. 7,381,205 to Thommen, a spring elastic guide wire within a tub having a spiral section displaces a distal end of a flexible catheter tube.

None of the above noted patents, nor any others observed by the applicant, demonstrate a surgical instrument with a flexible shaft being steered by upper and lower resilient members having a respective first end attached at the operation end of the surgical instrument, the upper and lower resilient members further slideably attached together having a second operational end being pulled upward or downward by the push or pull of the control trigger, causing the operational end of the surgical instrument to bend in an intended direction and degree, steering the operational end of the surgical instrument through tissue, the instrument being turned to steer the operational end in any intentional direction.

II. SUMMARY OF THE INVENTION

During a surgical procedure, surgical instruments comprising a handle and shaft portion and an application end are used by surgeons. These include cutting tools, suture passers, probes, grasping tools and clamps, among several. The insertion of these instruments is accomplished by either the tool cutting its own pathway, or the tools being inserted through a hole that is already cut through the tissue to the site of the surgical procedure. Quite often, this pathway is not a straight line, having the pathway directed around certain tissues as opposed to through them. This is difficult to accomplish using a rigid and straight instrument.

In some case, surgical instruments do include a curved portion at or near an end, or at least include an angled application end is provided. However, the pathway of the surgical instrument is restricted to the pathway being cut along the predetermined curved portion. Often tissue is unnecessarily damaged along the pathway due to having to insert and remove the surgical instrument to achieve the direction and angle desired to reach the site of the surgery from the external insertion point. It would be more suitable and less damaging to the collateral tissue if the surgeon had the ability to steer the surgical instrument, reducing the destruction of collateral tissue along the pathway, and actually have the ability to direct the surgical instrument at any desired angle or curve and in more than one direction.

The primary objective of the bi-directional steerable surgical instrument having a handle, a shaft and an operational end, more specifically a suture passer or cutting surgical instrument with a steerable mechanism, is to provide to surgical instrument with a resilient and intentionally flexible shaft of the surgical instrument with an upper and lower resilient member slideably engaged and forming a resiliently flexible shaft, both attached to a pivotal trigger near the application end and having a rear pulling extension and front pulling extension and pivotally attached to a handle of the surgical instrument, wherein the front and rear pulling extensions are pulled or pushed away from the application end, causing an intentional bend to the surgical instrument along the shaft to the second ends forming an operational end attached to a tool, either in an upward or downward direction, directing the operational end attached to the tool in a certain direction, the upper and lower resilient members retained together by tubing or a wrap attached along the upper and lower resilient members between the operational end and the pivotal trigger.

It is one of several objectives to provide a surgical instrument having an intentionally directed flexible shaft to reduce the amount of tissue damage during the insertion and use of the surgical instrument and the attached tool. It would also be an objective to provide the surgical instrument with the ability to be steered in more than one direction under the direct control of the surgeon to guide the tool on the operational end of the surgical instrument to a location intended by the surgeon. It is yet another objective to provide the surgical instrument with more than one tool on more than one set of upper and lower resilient members that may be easily exchanged by a medical professional to perform more than one procedure during a medical operation and also to replace the upper and lower resilient members and the tool attached to the second and operational ends of the resilient members for sanitary purposes and to avoid having to discard the entire surgical instrument after a singular use.

III. DESCRIPTION OF THE DRAWINGS

The following drawings are submitted with this utility patent application.

FIG. 3 is a right side view of the steerable surgical instrument.

FIG. 4 is a cross-sectional view along section lines 4/4 of FIG. 3.

FIG. 5 is an enlarged side view of the flexible shaft with the segmented lines indicating the upper and lower resilient members.

FIG. 6 is a right side view of the steerable surgical instrument with the front pulling extension pulled back, bending the flexible shaft in a downward direction.

FIG. 7 is a right side view of the steerable surgical instrument with the rear pulling extension pushed downward, bending the flexible shaft in an upward direction.

FIG. 8 is a left side view of the steerable surgical instrument being the reverse view of FIG. 3.

FIG. 9 is a side perspective view of the pivotal securing base.

FIG. 10 is an expanded component view of the steerable surgical instrument.

IV. DESCRIPTION OF THE PREFERRED EMBODIMENT

Figure 1:
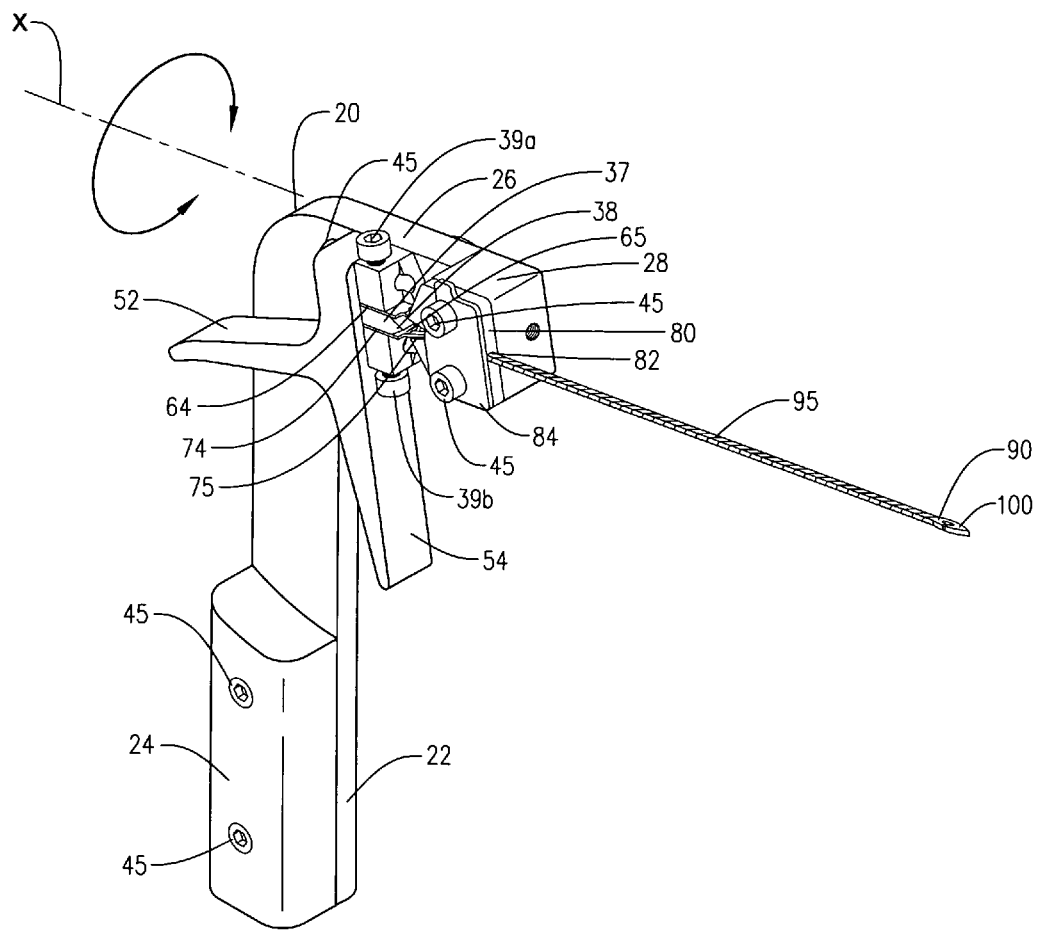
FIG. 1 is an upper right side perspective view of the steerable surgical instrument with a phantom reference line indicating the linear alignment of the flexible upper and lower resilient members forming the flexible shaft of the surgical instrument with the pivotal trigger in a neutral position.

A steerable surgical instrument 10, as illustrated in an embodiment shown in FIGS. 1-10, provides the surgical instrument with a steerable tip which may be guided through tissue in a pathway other than a simple linear pathway, the steerable surgical instrument 10 comprising a handle 20 defining a vertical shaft 22 with a lower grip portion 24 and a horizontal portion 26 forming a pivotal aperture 27 and a slide channel mounting section 28, a base anchor assembly bracket 30, FIGS. 9 and 10, having an inner surface 31 providing a cylindrical inner pivotal extension 32 and an outer aperture ring 33, FIG. 10 pivotally secured and installed within the pivotal aperture 27, a pivotal trigger mechanism 50 defining a rear trigger extension 52 and a front trigger extension 54 attached to a rear surface 35 of the base anchor assembly bracket 30, an upper resilient member 60 having a first end 62 defining a flat mounting tab 64 and a lowered transitional angled section 65, an extended flexible shaft 66 and a second end 68, a lower resilient member 70 having a first end 72 defining a flat mounting tab 74 and a raised transitional angled section 75, an extended flexible shaft 76 and a second end 78, the flat mounting tabs 64, 74 of the upper resilient member 60 and lower resilient member 70 secured within a mounting tab slot 36 within the base anchor assembly bracket 30 with a wedged separation member 37 located between the secured flat mounting tabs 64, 74, the wedged separation member 37 having a front wedged portion 38 contoured to the lowered and raised transitional angled sections 65, 75, a slide channel bracket 80 forming a slide channel 82 attached to the slide channel mounting section 28 of the handle, with a lower surface 67 of the extended flexible shaft 66 of the upper resilient member 60 slidingly engaging an upper surface 77 of the extended flexible shaft 76 of the lower resilient member 70, FIGS. 4 and 5, the extended flexible shafts 66, 76 being contained within the slide channel 82 by a slide channel plate 84, the extended flexible shafts 66, 76 retained together in slidable engagement with tubing 95 from the slide channel 82 to the second ends 68, 78, FIG. 4, the second ends 68, 78 of the upper and lower resilient members 60, 70 attached together forming an operational end 90 to which is further attached a surgical tool 100.

Figure 2:
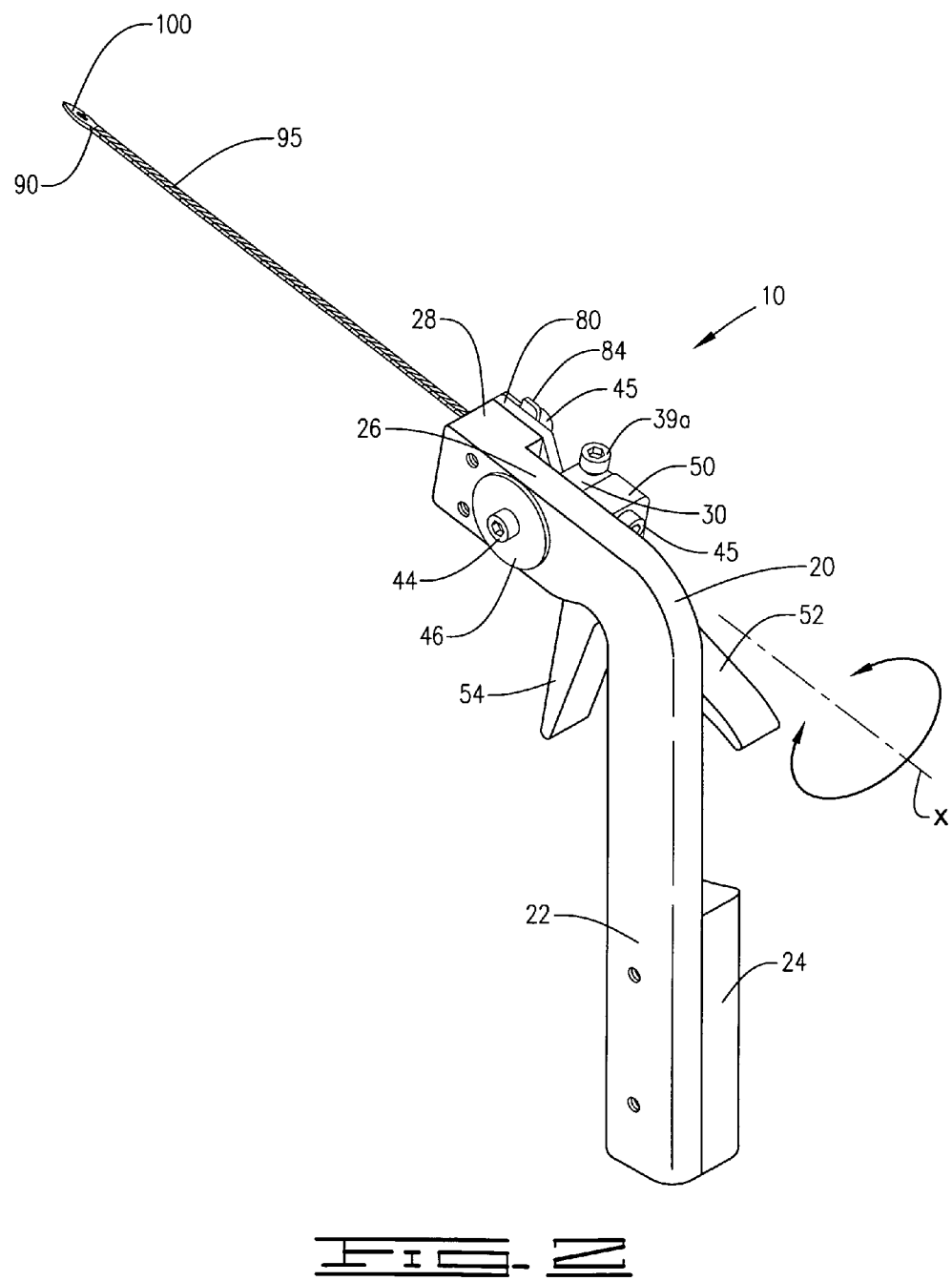
FIG. 2 is a reverse upper left side perspective view of the steerable surgical instrument shown in FIG. 1.

When the rear trigger extension 52 is pushed downward, FIG. 7, the base anchor assembly bracket 30 is pivoted counterclockwise causing a pulling force on the flat mounting tab 64 and the extended flexible shaft 66 of the upper resilient member 60 and applying a pushing force on the flat mounting tab 75 and the extended flexible shaft 76 of the lower resilient member 70, bending the extended flexible shafts 66, 76, the tubing 95, the operational end 90 and the attached tool 100 in an upward direction, in relation to a linear axis X as indicated in FIGS. 1 and 2. When the front trigger extension 54 is pulled back towards the handle 20, FIG. 6, the base anchor assembly bracket 30 is pivoted clockwise causing a pushing force on the flat mounting tab 64 and the extended flexible shaft 66 of the upper resilient member 60 and applying a pulling force on the flat mounting tab 74 and the extended flexible shaft 76 of the lower resilient member 70, bending the extended flexible shafts 66, 76, the tubing 95, the operational end 95 and the tool 100 in a downward direction in relation to the linear axis X as indicated in FIGS. 1 and 2. The steerable surgical instrument 10 thus provides the operational end 90 of the surgical instrument to be bent in an intended direction and degree, steering the operational end 90 of the surgical instrument 10 through tissue during a surgical procedure, the surgical instrument turned to steer the operational end 90 and tool 100 in any intentional direction as determined by the degree of rotation applied to the handle 20 during the surgical procedure in relationship to the linear axis X.

The pivotal trigger mechanism 50 is preferable removably attached to the rear surface 35 of the base anchor assembly bracket 30 by the use of screws 45, as indicated in FIG. 10, into the rear surface 35 of the base anchor assembly bracket 30. Likewise, the lower grip portion 24 may be attached to the vertical shaft 24 of the handle 20 by screws 45 threaded into the handle 20 and also the slide channel plate 84 being threadably attached through the slide channel bracket 80 into the slide channel bracket mounting section 28 of the handle 20. The cylindrical inner pivot extension 32 within the outer aperture ring 33 may be pivotally secured within the pivotal aperture 27 of the handle 20 by a single anchor base screw 44 and retaining washer 46, as indicated in FIGS. 2, 8 and 10, attached within a central threaded bore 34 of the cylindrical inner pivotal extension 32.

It is also preferred that the flat mounting tabs 64, 74 and the wedged separation member 37 be retained within the mounting tab slot 36 by an upper base screw 39a and lower base screw 39b, as best shown in FIGS. 1, 3 and 10, which threadably extend through the base anchor assembly bracket 30 onto the flat mounting tabs 64, 74, forcing them against the wedged separation member 37 from both an upper and lower direction. Installation of the upper and lower resilient members 60, 70, tubing 95 and tool 100 attached to the operational end 90 could be easily accomplished during a surgical procedure by loosening the upper and lower base screws 39a, 39b, placing the flat mounting tabs 64, 74 with the wedged separation member 37 between them into the mounting tab slot 36, engaging the extended flexible shafts 66, 76 of the upper and lower resilient members 60, 70 within the slide channel 82 of the slide channel bracket 80 and installing the slide channel plate 84, and tightening the upper and lower base screws 39a, 39b through the base anchor assembly bracket 30 onto the flat mounting tabs 64, 74, securing the upper and lower resilient members 60, 70 and the appropriate selected tool 100 within the steerable surgical instrument 10. Removal would be accomplished using the reverse procedure.

The upper and lower resilient members 60, 70 are preferably made of a flexible metal material with flat profiles, as indicated in the drawing figures, specifically FIGS. 4-5 and 10. It would be beneficial to the operation of the surgical instrument if the lower surface 67 of the extended flexible shaft 66 of the upper resilient member 60 and the lower surface 77 of the extended flexible shaft 76 of the lower resilient member 70 had a friction resistant coating to improve the ability of these contacting surfaces to slide against each other during operation of the trigger mechanism 50 to assist in the bending of these shafts during the surgical procedure. Additionally, the tubing 95 surrounding the two extended flexible shafts 66, 76 should not restrict the linear movement of the extended flexible shafts 66, 76, but yet prevent lateral disengagement of the extended flexible shafts 66, 76 and restrict separation of the two extended flexible shafts along their respective upper and lower surfaces 77, 67 of contact, as shown in FIGS. 4 and 5. The tubing 95 may be a wrap type material or a simple hollow tube, provided it meets the functional requirements above.

In the illustrations the surgical tool 100 is a suture passer with a cutting tip, but it is contemplated within the scope of the surgical instrument that it may be any penetrating or cutting surgical instrument. Using this installation and removal process may provide for the use of several paired upper and lower resilient members 60, 70 having different tools 100 during a single surgical procedure, allowing for multiple installation and removals of different paired upper and lower resilient members 60, 70 and tools 100, and also provide for disposable sets of upper and lower resilient members 60, 70 with various tools 100 while preserving the remainder of the steerable surgical instrument for repeated use. The steerable surgical instrument 10 is also disassembled into the components indicated in FIG. 10 for the purpose of complete sanitary cleansing subsequent to use during a surgical procedure to remove any and all contaminants and medical waste which may accumulate on the surgical instrument so that the surgical instrument may be used for another surgical procedure. It is also contemplated that the surgical instrument may be disposable if the surgical instrument may be manufactured and supplied at a sufficiently low cost, and made with relatively inexpensive materials.

By providing the steerable surgical instrument 10 in the disclosed embodiment having the ability to steer the operational end 90 and the tool 100 by the movement up or down in relationship to the linear axis X, the surgical instrument 10 may direct the tool 100 through tissue at a non-linear pathway, as is the case with other surgical instruments in the same filed of surgical art. The non-linear pathway will reduce the amount of damage to collateral tissue by being able to steer around the intervening tissue on the way to the site where the tool 100 is to be delivered to conduct the intended surgical activity with the attached tool 100 at an internal site, as opposed to having to cut or penetrate through the collateral tissue. This steerable surgical instrument 10 could be most beneficial in orthopedic surgical procedures, vascular surgical procedures, brain surgical procedures and an entire spectrum of other surgical procedures as a replacement, alternative or supplemental instrument used during the present surgical procedures.

While one or more embodiments of a steerable surgical instrument 10 has been particularly shown and described with reference to a preferred embodiment thereof, it will be understood by those skilled in the art of surgical instruments that changes in form and detail may be made therein without departing from the spirit and scope of the components and claims subject matter of the steerable surgical instrument.

What is claimed is:

1. A steerable surgical instrument provides a steerable tip which may be inserted through tissue during a surgical procedure in an intentionally linear or non-linear pathway, said steerable surgical instrument comprising:
   a handle providing a vertical shaft with a lower grip portion and a horizontal shaft defining a pivotal aperture and a slide channel mounting section along a linear axis;
   a base anchor assembly bracket defining an inner surface including a cylindrical pivotal extension emanating lateral from said inner surface, said cylindrical pivotal extension having a threaded bore and inserted within an outer aperture ring further inserted within said pivotal aperture, with an anchor base screw engaging said threaded bore through a washer through said handle, said base anchor assembly further defining a rear surface and a mounting tab slot;

a trigger mechanism attached to said rear surface of said base anchor assembly bracket by removable screws;

a slide channel bracket defining a horizontal slide channel attached to said slide channel mounting section;

an upper resilient member defining a first end having a flat mounting tab, a lowered transitional angled section, an extended flexible shaft having a lower surface and a second end and a lower resilient member defining a first end having a flat mounting tab, a raised transitional angled section, an extended flexible shaft having an upper surface and a second end, said flat mounting tabs held apart by a wedged separation member defining a front wedged-shaped portion and further secured within said mounting tab slot by an upper base screw and a lower base screw secured within said base anchor assembly bracket, with said lowered transitional angled section and said raised transitional angled section merging at said front wedged-shaped portion placing in contact the upper surface of the extended flexible shaft of the lower resilient member and the lower surface of the upper resilient member, said extended flexible shafts extending through said slide channel and slidably retained within said slide channel by a slide channel plate attached through said slide channel bracket into said slide channel mounting section of said handle, said extended flexible shafts surrounded by tubing from said slide channel bracket to said second ends, with said second ends of said upper and lower resilient members attaching to form an operational end attaching a surgical tool, wherein said trigger mechanism is rotated, a relative curvature relative to said linear axis is applied to said extended flexible shafts through said tubing, causing said operational end raised or lowered in relation to force applied to said trigger mechanism.

2. The steerable surgical instrument as disclosed in claim 1, wherein said trigger mechanism is rotatably forced counter-clockwise, said base anchor assembly bracket is pivoted causing a pulling force on said flat mounting tab and said extended flexible shaft of said upper resilient member and applying a pushing force on said flat mounting tab and said extended flexible shaft of said lower resilient member, bending the extended flexible shafts, the tubing and the operational end and the tool in an upward direction, in relation to said linear axis.

3. The steerable surgical instrument as disclosed in claim 1, wherein said trigger mechanism is rotatably forced clockwise, said base anchor assembly bracket is pivoted causing a pushing force on said flat mounting tab and said extended flexible shaft of said upper resilient member and applying a pulling force on said flat mounting tab and said extended flexible shaft of said lower resilient member, bending the extended flexible shafts, the tubing and the operational end and the tool in an downward direction, in relation to said linear axis.

4. The steerable surgical instrument as disclosed in claim 1, wherein said trigger mechanism is rotatably forced counter-clockwise, said base anchor assembly bracket is pivoted causing a pulling force on said flat mounting tab and said extended flexible shaft of said upper resilient member and applying a pushing force on said flat mounting tab and said extended flexible shaft of said lower resilient member, bending the extended flexible shafts, the tubing and the operational end and the tool in an upward direction, in relation to a linear axis; and wherein said trigger mechanism is rotatably forced clockwise, said base anchor assembly bracket is pivoted causing a pushing force on said flat mounting tab and said extended flexible shaft of said upper resilient member and applying a pulling force on said flat mounting tab and said extended flexible shaft of said lower resilient member, bending the extended flexible shafts, the tubing and the operational end and the tool in an downward direction, in relation to said linear axis.

5. The steerable surgical instrument as disclosed in claim 1, further comprising:

said upper and lower resilient members are made of a flexible metal material and having overall flat profiles with said lower surface of said extended flexible shaft of said upper resilient member and said lower surface of said extended flexible shaft of said lower resilient member having a friction resistant coating to improve the ability of said surfaces to slide upon each other during operation of said trigger to bend said flexible extension shafts during use; and said tubing surrounding said extended flexible shafts applied to avoid restriction of linear movement of said extended flexible shafts, while preventing lateral disengagement of said extended flexible shafts and restricting separation of said extended flexible shafts along said respective upper and lower surfaces of contact.

6. The steerable surgical instrument as disclosed in claim 1, wherein said tool may be selected from a list of surgical tools, including but not limited to a suture passer, a cutting tool, or any other penetrating or cutting instrument used in a surgical procedure.

7. A steerable surgical instrument provides a steerable tip which may be inserted through tissue during a surgical procedure in an intentionally linear or non-linear pathway, said steerable surgical instrument comprising:

a handle providing a vertical shaft with a lower grip portion and a horizontal shaft defining a pivotal aperture and a slide channel mounting section along a linear axis;

a base anchor assembly bracket defining an inner surface including a cylindrical pivotal extension emanating lateral from said inner surface, said cylindrical pivotal extension having a threaded bore and inserted within an outer aperture ring further inserted within said pivotal aperture, with an anchor base screw engaging said threaded bore through a washer through said handle, said base anchor assembly further defining a rear surface and a mounting tab slot;

a trigger mechanism defining a rear trigger extension and a front trigger extension attached to said rear surface of said base anchor assembly bracket by removable screws;

a slide channel bracket defining a horizontal slide channel attached to said slide channel mounting section;

an upper resilient member defining a first end having a flat mounting tab, a lowered transitional angled section, an extended flexible shaft having a lower surface and a second end and a lower resilient member defining a first end having a flat mounting tab, a raised transitional angled section, an extended flexible shaft having an upper surface and a second end, said flat mounting tabs held apart by a wedged separation member defining a front wedged-shaped portion and further secured within said mounting tab slot by an upper base screw and a lower base screw secured within said base anchor assembly bracket, with said lowered transitional angled section and said raised transitional angled section merging at said front wedged-shaped portion placing in contact the upper surface of the extended flexible shaft of the lower resilient member and the lower surface of the upper resilient member, said extended flexible shafts extending through said slide channel and slidably retained within said slide channel by a slide channel plate attached through said slide channel bracket into said slide channel mounting section of said handle, said extended flexible shafts surrounded by tubing from said slide channel bracket to said second ends, with said second ends of said upper and lower resilient members attaching to form an operational end attaching a surgical tool, wherein said trigger mechanism is moved, a relative curvature relative to said linear axis is applied to said extended flexible shafts through said tubing, causing said operational end raised or lowered in relation to said force applied to said trigger mechanism.

8. The steerable surgical instrument as disclosed in claim 7, wherein said rear trigger extension is forced downward, said base anchor assembly bracket is pivoted causing a pulling force on said flat mounting tab and said extended flexible shaft of said upper resilient member and applying a pushing force on said flat mounting tab and said extended flexible shaft of said lower resilient member, bending the extended flexible shafts, the tubing and the operational end and the tool in an upward direction, in relation to said linear axis.

9. The steerable surgical instrument as disclosed in claim 7, wherein said front trigger extension is pulled backwards, said base anchor assembly bracket is pivoted causing a pushing force on said flat mounting tab and said extended flexible shaft of said upper resilient member and applying a pulling force on said flat mounting tab and said extended flexible shaft of said lower resilient member, bending the extended flexible shafts, the tubing and the operational end and the tool in an downward direction, in relation to said linear axis.

10. The steerable surgical instrument as disclosed in claim 7, wherein said rear trigger extension is forced downward, said base anchor assembly bracket is pivoted causing a pulling force on said flat mounting tab and said extended flexible shaft of said upper resilient member and applying a pushing force on said flat mounting tab and said extended flexible shaft of said lower resilient member, bending the extended flexible shafts, the tubing and the operational end and the tool in an upward direction, in relation to a linear axis; and wherein said front trigger extension is pulled backwards, said base anchor assembly bracket is pivoted causing a pushing force on said flat mounting tab and said extended flexible shaft of said upper resilient member and applying a pulling force on said flat mounting tab and said extended flexible shaft of said lower resilient member, bending the extended flexible shafts, the tubing and the operational end and the tool in an downward direction, in relation to said linear axis.

11. The steerable surgical instrument as disclosed in claim 7, further comprising:

said upper and lower resilient members are made of a flexible metal material and having overall flat profiles with said lower surface of said extended flexible shaft of said upper resilient member and said lower surface of said extended flexible shaft of said lower resilient member having a friction resistant coating to improve the ability of said surfaces to slide upon each other during operation of said trigger to bend said flexible extension shafts during use; and said tubing surrounding said extended flexible shafts applied to avoid restriction of linear movement of said extended flexible shafts, while preventing lateral disengagement of said extended flexible shafts and restricting separation of said extended flexible shafts along said respective upper and lower surfaces of contact.

12. The steerable surgical instrument as disclosed in claim 7, wherein said tool may be selected from a list of surgical tools, including but not limited to a suture passer, a cutting tool, or any other penetrating or cutting instrument used in a surgical procedure.

* * * * *